United States Patent [19]

Berber et al.

[11] 4,193,288

[45] Mar. 18, 1980

[54] APPARATUS FOR CALIBRATING INSTRUMENTS FOR GRANULOMETRIC RECORDING

[76] Inventors: Viktor A. Berber, ulitsa Shelkovichnaya, 184, kv. 65; Evgeny S. Pervushin, ulitsa Shelkovichnaya, 182, kv. 71; Khafiz M. Murtazin, 6 Internatsionalny proezd, 20; Vladimir G. Kholin, ulitsa Shelkovichnaya, 184, kv. 53; Boris M. Galishnikov, ulitsa Shelkovichnaya, 190, kv. 27, all of Saratov, U.S.S.R.

[21] Appl. No.: 935,502

[22] Filed: Aug. 21, 1978

[51] Int. Cl.² ............................................. G01N 15/00
[52] U.S. Cl. .................................... 73/1 R; 73/432 PS
[58] Field of Search ............... 73/1 R, 53, 56, 432 PS; 209/586; 356/102, 243

[56] References Cited

U.S. PATENT DOCUMENTS

| | | | |
|---|---|---|---|
| 3,669,542 | 6/1972 | Capellaro | 356/243 X |
| 3,791,192 | 2/1974 | Butler | 73/1 R |
| 3,869,208 | 3/1975 | Lorenz | 356/102 |
| 3,908,465 | 9/1975 | Bartlett | 73/432 PS |

*Primary Examiner*—Donald Watkins
*Attorney, Agent, or Firm*—Fleit & Jacobson

[57] ABSTRACT

An apparatus for producing a fluid flow containing particles of a given size is intended to calibrate the instruments for granulometric recording of particles in fluids. The apparatus comprises a chamber having an inlet port and an outlet duct to communicate with the inlet of the instrument being calibrated, and having a feeding duct to feed the chamber with reference particles. At least one portion of the chamber near the outlet duct is implemented as a horizontally oriented transparent cylinder in which a transparent duct is disposed coaxially with the cylinder. One end portion of the transparent duct tapers to a diametrical size which is commensurate with the maximum diameter of the reference particles. An inspection means to monitor the size of the reference particles is disposed above this end portion. The other end portion of the transparent duct is isolated from the chamber cavity and communicates with the feeding duct which is provided with an adjustable reverse pumping means capable of pumping the fluid with the reference particles through the feeding duct and the transparent duct.

2 Claims, 4 Drawing Figures

APPARATUS FOR CALIBRATING INSTRUMENTS FOR GRANULOMETRIC RECORDING

FIELD OF THE INVENTION

The invention relates to measuring systems, and more particularly to apparatus for producing a fluid flow containing particles of a given size, adapted to calibrate the instruments for granulometric recording of particles in fluids such as motor fuels and oils.

DESCRIPTION OF THE PRIOR ART

Known in the art is a device for producing a fluid flow containing particles of a given size, designed to calibrate the instruments for granulometric recording of particles in fluids, said device comprising a chamber made as a vertical cone-shaped funnel having an inlet port and an outlet duct adapted to communicate with the inlet of the instrument being calibrated, said chamber being provided with a means for pumping uncontaminated fluid through it and with a duct to feed it with reference particles.

This device can utilize, however, only monodisperse reference particles, i.e., identical particles of a predetermined size, for calibration of the instruments. Granulometric recording of contamination particles in fluids requires that particles of different size be handled. It is therefore necessary to have a set of monodisperse reference particles for calibration of the granulometric recording instruments. Each group of the reference particles of the set must include particles of the same size and the number of such groups must correspond, as a minimum, to the number of the working ranges of the instrument being calibrated. For example, five or more ranges are available in the instruments that deal with contamination particles in fuels and oils. As a result, at least five groups of reference particles of different size for each group must be provided and each group must include particles of the same size equal, for example, to the average particle size of a respective range.

In addition, the reference particles must be made of different materials corresponding to the materials of contamination particles in order to determine the influence given by the latter materials on the readings of the instruments.

The described set of several groups of monodisperse reference particles is difficult to produce. At present, no completed sets of this type are known which could provide for the calibration curve of adequate validity, namely, the curve that describes a relationship between the magnitude of the wanted signal and the diameter of the particles being recorded.

Note that the calibration of the instruments with the help of the sets of monodisperse reference particles requires much labor since uncontaminated fluid must be first pumped through the calibration device and the instrument being calibrated so as to obtain zero readings of the instrument. After that, the first group of the reference particles is introduced into the funnel, is stirred up thoroughly and is passed through the instrument being calibrated together with the fluid. After the magnitude of the wanted signal has been recorded, a single point of the calibration curve is obtained. Now, uncontaminated fluid is pumped through the overall system to remove the particles of the first group, zero readings of the instrument being calibrated are obtained, the particles of the second group are introduced into the funnel and so on.

Considerable simplifications can be attained with sets of polydisperse reference particles in which a mixture of particles of all sizes available belongs to each reference group. These sets cannot be used, however, with the described calibration device since one cannot establish the correspondence between the signals produced by the instrument being calibrated and the size of the particles involved.

SUMMARY OF THE INVENTION

An object of the invention is to provide an increased validity and productivity in calibrating instruments designed for granulometric recording of particles in fluids.

There is disclosed an apparatus for producing a fluid flow containing particles of a given size, adapted to calibrate instruments for granulometric recording of particles in fluids and comprising a chamber having an inlet port and an outlet duct adapted to communicate with the inlet of the instrument being calibrated, the chamber being provided with a means to pump uncontaminated fluid through it and with a feeding duct to feed it with reference particles, said apparatus being provided, according to the invention, with at least one chamber portion of the chamber, located near the outlet duct and implemented as a horizontally positioned transparent cylinder in which a transparent duct is disposed coaxially with the cylinder and has one end portion tapering to a diametrical size which is commensurate with the maximum diameter of the reference particles, an inspection means to monitor the size of the reference particles being disposed above the end portion and outside of the chamber, the transparent duct being provided with the other end portion which is isolated from the cavity of the chamber and communicates with the feeding duct, the latter being provided with an adjustable reverse pumping means capable of pumping the fluid with the reference particles through the feeding duct and the transparent duct.

Advantageously, the feeding duct is positioned not lower than the lower inner wall of the transparent duct so as to prevent the loss, within the apparatus proper, of the reference particles capable of providing wanted information.

The apparatus of the invention provides for an increased validity and productivity in calibrating the instruments for granulometric recording of particles in fluids due to the fact that polydisperse reference particles are used which are mixtures of spherical particles of different size. These mixtures, as compared to monodisperse ones, are easy to produce. Higher calibration validity is attained since a mixture of polydisperse particles includes a complete set of particles of all sizes available so that the total working range of the instrument being calibrated is involved in calibration. The calibration curve can be plotted in this case using a great number of points and good validity is therefore achieved.

In addition, the apparatus of the invention can be operated to prevent the loss in it of the reference particles capable of providing wanted information.

DESCRIPTION OF THE DRAWINGS

The invention will now be described, by way of example, with reference to the accompanying drawings in which.

DESCRIPTION OF THE INVENTION

Figure 1:
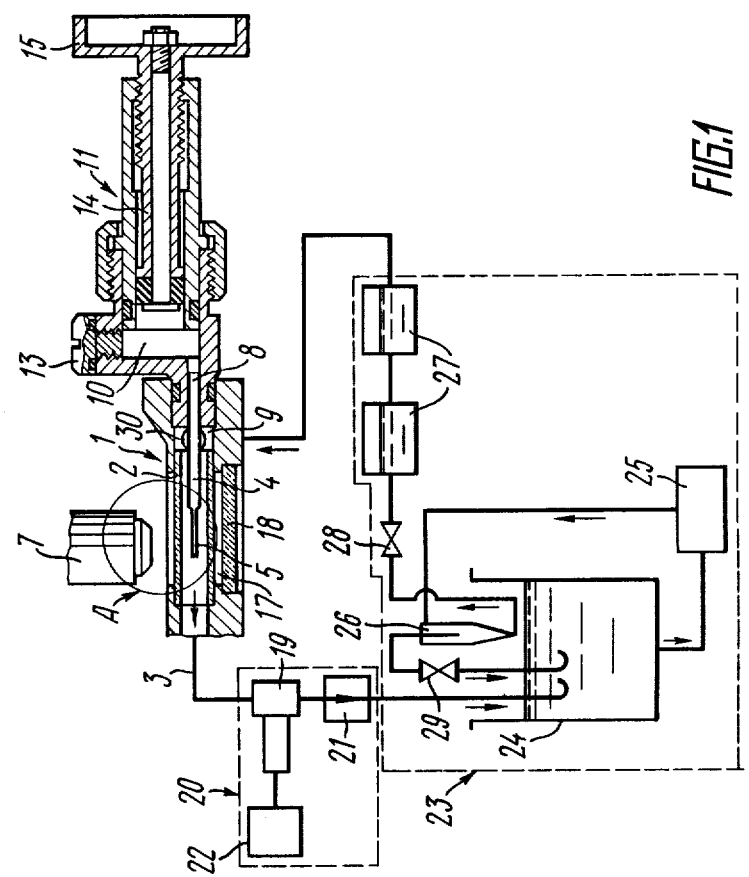
FIG. 1 is a diagrammatical representation of the design of an apparatus for producing a fluid flow containing particles of a given size, according to the invention.
Figure 2:
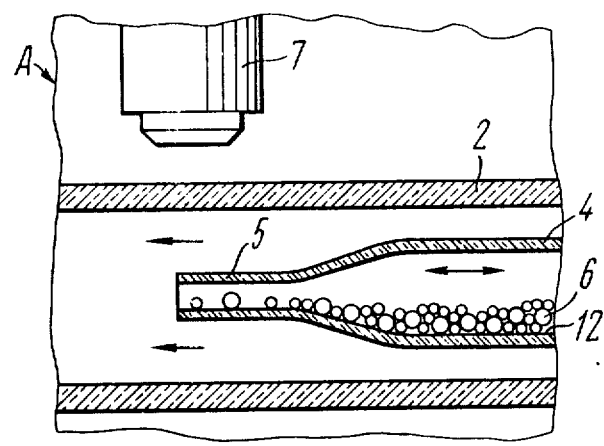
FIG. 2 shows the portion A of FIG. 1, on an enlarged scale, according to the invention.
Figure 3:
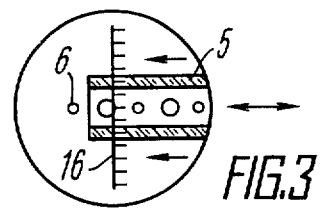
FIG. 3 is a top view of the tapering end portion of the transparent duct as observed through a microscope, according to the invention.

The apparatus according to the instant invention (FIGS. 1,2,3) comprises a chamber 1 whose chamber portion 2 near the outlet duct 3 (shown in solid line) is implemented as a horizontally oriented transparent cylinder in which a transparent duct 4 is disposed coaxially with the cylinder. An end portion 5 of the transparent duct 4 tapers to a diametrical size which is commensurate with the maximum diameter of reference particles 6 (FIGS. 2,3).

An inspection means 7 to monitor the size of the reference particles 6 is disposed above the end portion 5 and outside of the chamber 1. The other end portion 8 (FIG. 1) of the transparent duct 4 is isolated from a cavity 9 of the chamber 1 and communicates with a feeding duct 10 to feed the chamber 1 with the reference particles 6. The feeding duct 10 is provided with an adjustable reverse pumping means 11 capable of pumping the fluid with the reference particles 6 through the feeding duct 10 and the transparent duct 4.

To prevent the loss, in the apparatus proper, of the reference particles 6 capable of providing wanted information, the bottom of the feeding duct 10 is located at the level of a lower wall 12 (FIG. 2) of the transparent duct 4. The feeding duct 10 is provided with a port 13 (FIG. 1) through which the reference particles 6 are fed.

The adjustable reverse pumping means 11 which provides for the pumping of the fluid with the reference particles 6 through the feeding duct 10 and the transparent duct 4 serves to displace the fluid with the reference particles 6 from the transparent duct 4, via the tapering end portion 5, into the chamber portion 2 of the chamber 1. To this end, the means 11 has a piston 14 controlled by a knob 15 which is rotated to move the piston 14 in the required direction.

To provide for good sharpness of the image of the end portion 5 of the transparent duct 4 in the field of vision of the inspection means 7 (a microscope with a measuring scale 16, FIG. 3), the chamber 1 (FIG. 1) has a recess 17 surrounding the chamber portion 2, having a transparent plate 18 on its under side and filled with a fluid whose refractive index has its value close to the refractive index of the material of the chamber portion 2. The outlet duct 3 communicates with the input of a sensor 19 of the instrument 20 being calibrated, whereas the output of the sensor 19 is coupled to a flow regulator 21. The sensor 19 is coupled electrically to an indicator 22.

A means 23 to pump uncontaminated fluid through the chamber 1 has a vessel 24 to contain the fluid, a unit 25 which is a cleaning pump implemented as a thin layer centrifuge with a pressure disc, an air bubble separator 26 and fluid flutter dampers 27. The air bubble separator 26 is a hydrocyclone means. The fluid flutter dampers 27 are vessels with submerged inlets and outlets above which an air cushion is produced to kill the fluid flutter.

Cocks 28, 29 are used to regulate the fluid flow. The means 23 is connected with the chamber 1 via its inlet port 30 having its axis disposed at right angles to the axis of the chamber portion 2.

The disclosed apparatus operates in the following manner.

The means 23 is operated to fill the hydraulic system of the apparatus with uncontaminated fluid. The port 13 is opened and a portion of the polydisperse reference particles 6 is delivered to the feeding duct 10 and the particles 6 tend to sink on to the bottom of the duct 10. After that, the particles 6 spread over the duct 4 and assume a position shown in FIG. 2. The port 13 is closed. During this procedure, check to see that no air bubbles occur under the port 13 since otherwise they cause the flutter of the fluid flow being delivered from the means 11 to the transparent duct 4. This flutter, if any, affects the measurement of the particles 6 in the end portion 5 of the transparent duct 4.

Figure 4:
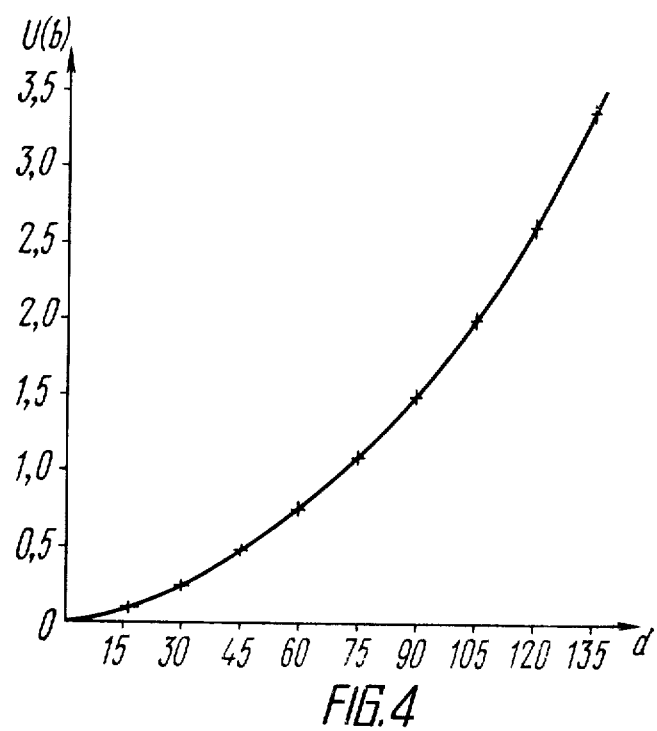
FIG. 4 is an example of a calibration curve, according to the invention.

Uncontaminated fluid is then pumped continuously through the chamber portion 2 (the direction of the fluid flow is shown by arrows) until the indicator 22 reads zero. The indicator 22 is an oscilloscope or a digit-type pulsed voltmeter. Turning the knob 15 causes the piston 14 to move to the left (as shown in the drawing) with the result that the fluid is led out of the ducts 10 and 4 via the tapering end portion 5 into the portion 2 of the chamber 1. The liquid, in the course of its movement, carries the reference particles 6 together with it and they roll over the bottom of the tapering end portion 5 along a single line in a one-by-one fashion so as to appear in the field of vision of the inspection means 7. At this moment, the rotation of the knob 15 is stopped and the piston 14 ceases to move; also, the reference particles 16 stop moving in the end portion 5. Using the measuring scale 16 of the inspection means 7 (FIG. 3), the diameter of the first particle is measured. The knob 15 is then rotated a little with the result that the piston 14 is moved to the left (as shown in the drawing) and the first particle of the reference particles 6 is driven by the fluid from the end portion 5 to the chamber portion 2. The first particle is then introduced into the flow of uncontaminated fluid and is transferred to the sensor 19 via the outlet duct 3. The second particle of the reference particles 6 is left within the end portion 5. When the first particle passes through the sensor 19 a signal is produced therein which is sensed by the indicator 22. After that, the second particle is measured and introduced into the fluid flow, etc. The measurement results are used to plot a calibration curve (FIG. 4) which describes how the magnitude of wanted signal changes with the particle diameter. In FIG. 4, the pulsed voltage in volts is plotted on the X axis and the particle diameter in μm is plotted on the Y axis.

The means 11 (FIGS. 1,2,3) allows, to a certain extent, for the selection of a portion of the reference particles 6 from the entire particle mass contained in the transparent duc 4 so that the calibration curve can be constructed. For this, the piston 14 is moved alternatively to the right and to the left at various speeds. With the piston 14 moved to the right, uncontaminated fluid is led from the chamber portion 2, via the end portion 5, into the transparent duct 4 and carries together with it the reference particles 6 so that they are driven out of the end portion 5. With the piston 14 moved to the left, new particles 6 arrive at the end portion 5. If these particles 6 are of the required size they are measured and are then passed to the portion 2, etc.

The calibration curve so obtained is used to adjust the working ranges of the calibrated instrument for granulometric recording of particles in fluids.

When carried by the fluid flow, the reference particles 6 pass through the sensor 19 and the flow regulator 21 to enter the vessel 24 from which the fluid with the reference particles 6 is sucked up by the pump of the unit 25 and the particles 6 are filtered out in it so that only uncontaminated fluid is allowed to pass into the chamber 1.

With the apparatus of the invention, the measured reference particles 6 can be introduced into the flow of uncontaminated fluid not only in the one-by-one fashion described above but also in groups. To this end, the flow regulator 21 is operated to stop the fluid flow completely. A preset amount of the reference particles 6 previously measured is delivered from the end portion 5 of the transparent duct 4 into the chamber portion 2 and the resulting data is noted. Since no flow of uncontaminated fluid is available, these particles 6, after leaving the end portion 5, tend to sink onto the bottom of the chamber portion 2. With the flow regulator 21 open, the fluid flow is given the particles 6 and carries them into the sensor 19 and further into the vessel 24. The sensor 19 provides the indicator 22 with respective signals. In this case, the indicator 22 must be a means capable of recording the size and amount of the particles 6 moved in the fluid flow. The data available from the indicator 22 are compared to the noted initial data describing the size and amount of the particles 6, which allows for the determination of the accuracy of the instrument being calibrated, concerned with the size and amount of the particles 6.

The flow regulator 21 is set at the output of the sensor 19 in order to prevent the foreign particles resulted from the friction process in the flow regulator 21 from getting into the sensor 19.

The apparatus of the invention is basically intended for calibration methods based on solid reference particles whose density exceeds that of the fluid. After entering the feeding duct 10, the particles 6 tend to spread over the transparent duct 4, as shown in FIG. 2. The maximum working volume of the transparent channel 4, as related to the reference particles 6 and used to determine the amount of them to be fed, is attained in a condition when the free horizontal surface of the mass of the particles 6 is oriented tangentially to the lower wall of the tapering end portion 5. When a portion of the reference particles 6 exceeds the preset amount, the excessive particles 6 pass into the portion 2 and cannot be effective.

An enormous increase in the diameter of the transparent duct 4 so as to provide for a greater amount of a single portion of the reference particles 6 being fed is not recommended since a greater speed of the fluid flow carrying the particles with the help of the means 11 is required and the particles 6 passing through the tapering end portion 5 cannot be observed in this case.

A single portion of the reference particles 6 makes it possible to plot several tens of calibration curves.

What is claimed is:

1. An apparatus for producing a fluid flow containing reference particles of a given size, adapted to calibrate instruments for granulometric recording of particles in fluids and comprising:
   a chamber;
   an inlet port of said chamber;
   an outlet duct of said chamber adapted to communicate with the inlet of the instrument being calibrated;
   a means to pump uncontaminated fluid through said chamber;
   a feeding duct to feed said chamber with said reference particles;
   at least one chamber portion of said chamber, located near said outlet duct and implemented as a horizontally positioned transparent cylinder;
   a transparent duct disposed within said transparent cylinder coaxially therewith;
   one end portion of said transparent duct tapering to a diametrical size which is commensurate with the maximum diameter of said reference particles;
   an inspection means to monitor the size of said reference particles, disposed above said tapering end portion and outside of said chamber;
   the other end portion of said transparent duct, isolated from the cavity of said chamber and adapted to communicate with said feeding duct;
   an adjustable reverse pumping means capable of pumping the fluid with said reference particles through said feeding duct and said transparent duct.

2. An apparatus as claimed in claim 1, comprising said feeding duct located not lower than the lower inner wall of said transparent duct.

* * * * *